United States Patent [19]
Dillow

[11] Patent Number: 5,419,324
[45] Date of Patent: May 30, 1995

[54] RADIOLOGICAL MARKER BOARD WITH MOVABLE INDICATORS

[75] Inventor: David C. Dillow, Cupertino, Calif.
[73] Assignee: EndoVascular Technologies, Inc., Menlo Park, Calif.
[21] Appl. No.: 157,703
[22] Filed: Nov. 24, 1993
[51] Int. Cl.⁶ .......................... A61B 5/00; A61B 19/00; G03B 42/02
[52] U.S. Cl. .................... 128/653.1; 378/163; 378/208
[58] Field of Search ............... 128/653.1, 653.2, 653.5; 378/163, 164, 205, 208

[56] References Cited

U.S. PATENT DOCUMENTS

| | | |
|---|---|---|
| 2,790,084 | 4/1957 | O'Dell et al. |
| 3,547,121 | 12/1970 | Cherry |
| 3,812,842 | 5/1974 | Rodriguez |
| 4,127,774 | 11/1978 | Gillen ............................ 378/205 |
| 4,187,423 | 2/1978 | Ehrhardt |
| 4,279,252 | 7/1981 | Martin |
| 4,698,836 | 10/1987 | Minasian ........................ 378/205 |
| 4,838,265 | 6/1989 | Cosman et al. |
| 4,860,331 | 8/1989 | Williams et al. |
| 4,878,115 | 10/1989 | Elion |
| 4,915,112 | 4/1990 | Singer .......................... 128/653.1 |
| 4,916,725 | 4/1990 | Quinter et al. ................. 378/205 |
| 5,052,035 | 9/1991 | Krupnick |
| 5,068,886 | 11/1991 | Lavia |
| 5,211,683 | 5/1993 | Maginot |
| 5,216,700 | 6/1993 | Cherian ......................... 378/163 |
| 5,222,115 | 6/1993 | Highgenboten ................. 378/205 |

OTHER PUBLICATIONS

Jonathan Tobis, MD et al., Am. J Cardiol (1985); pp. 56:237-241, "Digital Coronary Roadmapping as an Aid for Performing Coronary Angioplasty".

*Primary Examiner*—Krista M. Pfaffle
*Attorney, Agent, or Firm*—Fulwider Patton Lee & Utecht

[57] ABSTRACT

A system is disclosed for locating positions in the vasculature of a human patient for the purpose of rendering treatment or making a diagnosis therein during a catheterization procedure, such as a procedure to implant an intraluminal arterial graft. The system includes a board which rests under the patient during the procedure which has two markers that can be detected under fluoroscopy. The markers can be moved backwards and forwards along a track in the board to pinpoint various locations in the blood vessel of interest, for example, the points of attachment for the ends of an arterial graft. One of the markers also can be pivoted about the track to represent the angle at which a particular blood vessel is disposed in the patient. The markers can be locked into position with brakes for the duration of the procedure.

21 Claims, 5 Drawing Sheets

RADIOLOGICAL MARKER BOARD WITH MOVABLE INDICATORS

BACKGROUND OF THE INVENTION

The invention generally is related to a marker system for locating positions within the blood vessels of a patient so that diagnosis can be made at or between the positions or so that treatment can be rendered there. More particularly, the invention is a marker system with one or more indicators that can be visualized under X-ray imaging, for example radiography or fluoroscopy, while treatment or diagnosis is undertaken using catheters or other instruments inserted into the vasculature, such as when an intraluminal graft is being implanted, to guide the placement of the catheter or instruments.

Catheters long have been used for the purpose of diagnosing anomalous conditions in the vasculature or for rendering treatment therein. For example, catheters have been used to deploy grafts, to remove occlusions and to expand areas affected by arteriosclerosis. Procedures employing catheters are attractive because use of catheters avoids more surgically invasive procedures, minimizing the risks to the patient.

The effectiveness of any catheterization procedure heavily depends on the ability of the clinician to accurately locate the area of the vasculature at which a diagnosis is to be made or treatment is to be rendered. Various systems and methods have been proposed to facilitate this location process. Most involve fluoroscopic visualization of the vasculature using a radiopaque dye with a catheter equipped with radiopaque tags, which tags also can be detected by radiographic means. Because radiopaque dye injected into the blood vessels quickly is dispersed through action of the circulatory system, the clinician heretofore has had to rely on the clinician's recollected image of the almost instantaneous visualization of the blood vessels in order to pinpoint the site at which diagnosis or treatment is to take place.

Recently, computerized digital substraction technology, colloquially known as "roadmapping," has been developed to aid the clinician's memory. This technique effectively takes a picture of the fluoroscopic image of the blood vessels when the vessels are illuminated by the radiopaque dye and uses a computer to digitize the image. The digitized image then can be superimposed over an analog, "real time" image that tracks the progress of a radiopaque-tipped catheter through the vasculature. This technique greatly reduces the clinician's need to rely on the clinician's memory to target the approximate site at which diagnosis or treatment is to take place. However, the technique does not allow the clinician to precisely mark where within a particular vessel a procedure is to be performed.

Catheter systems are especially well-suited for deploying arterial grafts to an area within the abdominal aorta which is affected by an aneurysm, in order to relieve pressure on the vessel walls. An aneurysm is a bulged area of a vessel that is caused by genetic defects or, more commonly, by disease that might or might not be a result of genetics such as arteriosclerosis. If the pressure at the aneurysm is not relieved by some means, the vessel might rupture. Grafts often are placed at the location of aneurysms to create an artificial passageway for blood flow, so the blood pressure is sustained by the graft and not the wall of the vessel. A frequent site of occurrence of abdominal aortic aneurysms is the portion of the aorta just caudal to the branch point of the renal arteries. In a typical procedure to locate an aneurysm, the clinician can identify the site at which a graft is to be deployed by using fluoroscopy or other radiography techniques. This identification step can be accomplished with the technique of X-ray film subtraction or, more modernly, with the technique of Digital Subtraction Angiography (DSA).

In DSA, a catheter is inserted into a blood vessel in the area of interest and a baseline or pre-injection image is captured using an X-ray source, an X-ray image intensifier, a fluoroscopic television, and a computer. The image is digitized and then stored by the computer. Then a bolus of dye containing iodine or another substance that readily can be visualized under fluoroscopy is injected through the catheter and another radiographic image or rapid series of images is captured, digitized and stored while the dye is present in the vessels of interest and before it has dissipated through the bloodstream. The computer subtracts the pre-injection image from the images acquired just after injection, performs some enhancement operations, and produces a static digital image of the blood vessels. A more time consuming but sometimes more accurate process of film subtraction involves superimposing a pre-injection X-ray film on a post-injection X-ray film to produce a static image.

After the static image has been obtained, the catheter used in the procedure to obtain it might be removed in order to insert a second catheter bearing the intraluminal graft to be implanted. Alternatively, the in-place catheter already may be carrying the graft. The catheter used to carry the graft to the implantation site usually has a distal end configured to allow the catheter to negotiate the anatomy of the vascular system. The graft then can be delivered by anchoring the ends of the graft to the vessel wall, such as with hooks attached to the graft. Thus, when the catheter is removed, the graft remains in place, and provides a passageway for the blood to move through without applying any pressure to the aneurysm.

In order for the graft to effectively perform its pressure relieving function, it is critical that the graft be implanted so that it extends along the full length of the aneurysm. Identifying where the anchoring systems should be placed is difficult when the clinician only has radiographic subtraction techniques upon which to rely. Such techniques merely guide the clinician to the approximate area of the vasculature in which the aneurysm appears. The techniques do not allow identification of where the proximal and distal ends of the graft should be affixed.

What is needed and has heretofore been unavailable then, is a marker system that can be used with existing radiographic techniques for locating particular positions within the blood vessels of a patient, to allow a clinician to accurately place a graft at the site of an aneurysm, or to render other treatment or perform a diagnosis at an affected site in the vasculature. The present invention fulfills this need.

SUMMARY OF THE INVENTION

The invention herein disclosed is particularly well suited for use in a clinical procedure to implant an intraluminal graft at the site of an aneurysm in a blood vessel of a patient, because it facilitates the ability of the clinician to accurately place the grafts using techniques such as radiography or fluoroscopy. The marker system includes a body, such as a multilayer board, having one or more radiopaque markers. The markers are movable along a track in a recessed area within a first layer of the board.

Each radiopaque marker is attached to a positioner, such as a control cable, which may extend exterior of the board. Each marker preferably has a width greater than the width of the track so that the marker rests on top of, rather than inside of, the track. Constant force springs or similar biasing devices may be attached to the markers to move the markers in cooperation with the positioner or control cable. A second layer preferably is mounted over the first layer of the body to cover and protect each marker and each control cable. As no marker extends above the recessed area in the first layer, the second layer does not inhibit the marker or markers from moving along the track.

In a marker system with at least two markers, one marker is configured with a pivot. A pair of control cables is attached to the pivotable marker to allow the clinician to set the position and angle of the marker. A pivotable marker is very useful when the patient's anatomy is non-standard due to genetic factors or other physiological conditions, such as when the abdominal aorta is canted laterally. A pivoting marker can be positioned to reflect that the vessel is so affected at the point where one of the anchoring systems for the graft is to be attached.

The marker system also can be provided with one or more brakes, for example, in the first layer of the board, to allow the clinician to temporarily lock each marker into a particular position along the track. A separate brake can be provided for each control cable. Alternatively, a single brake can be provided for a pair of control cables that are attached to a pivotable marker. The brakes may be locked and unlocked with brake cables which may extend exterior of the board. Alternatively, the brakes may be housed externally of the marker board body, such as in a control box used for actuating the control cables.

For ease of use, the control cables and the brake cables are preferably connected outside the marker board body to a control box. The control box includes knobs that are attached to each control cable and each brake cable to push the cables towards the board or to pull the cables towards the clinician. In this manner, the markers are moved along the track and the brakes are locked and unlocked. Alternatively, concentric wheels may be used to coil and uncoil the control cables, and a braking system housed in the control box may be used to hold or fix the markers in place.

In use, the board is located under a patient positioned on an operating table. The board is positioned in the area where the aneurysm is located. During the procedure, a catheter bearing an intraluminal graft is advanced through the vasculature to the affected vessel. Subtracted X-ray film or digital images obtained in an earlier angiographic procedure then are relied upon to identify the location or locations at which a graft is to be deployed. This step usually involves using the point at which the renal arteries branch from the abdominal aorta as a point of reference. Since both the catheter and each marker have radiopaque elements, the relative positions of the graft and the marker or markers can be observed under fluoroscopy by the clinician. After the initial fluoroscopic images have been taken and a subtraction technique has been used to visualize the blood vessels, the control cables are manipulated to orient each marker in a position or positions which correspond to the point or points in the vessel at which the anchoring systems for the graft are to be attached. When the graft is properly positioned at the marker or markers, the graft can be anchored to the vessel wall to alleviate the pressure at the aneurysm.

As can be understood from the foregoing, the system of the invention allows a clinician to precisely identify the area within a blood vessel at which some procedure is to be performed, such as the implantation of an arterial graft, by providing an indication of the upper and lower bounds of the treatment site with markers visible under fluoroscopy. This and other features and advantages of the invention will become more apparent from the following detailed description taken in conjunction with the accompanying exemplary drawings, which illustrate by way of example the principles of the invention.

DETAILED DESCRIPTION OF THE PREFERRED EMBODIMENTS

Figure 1:
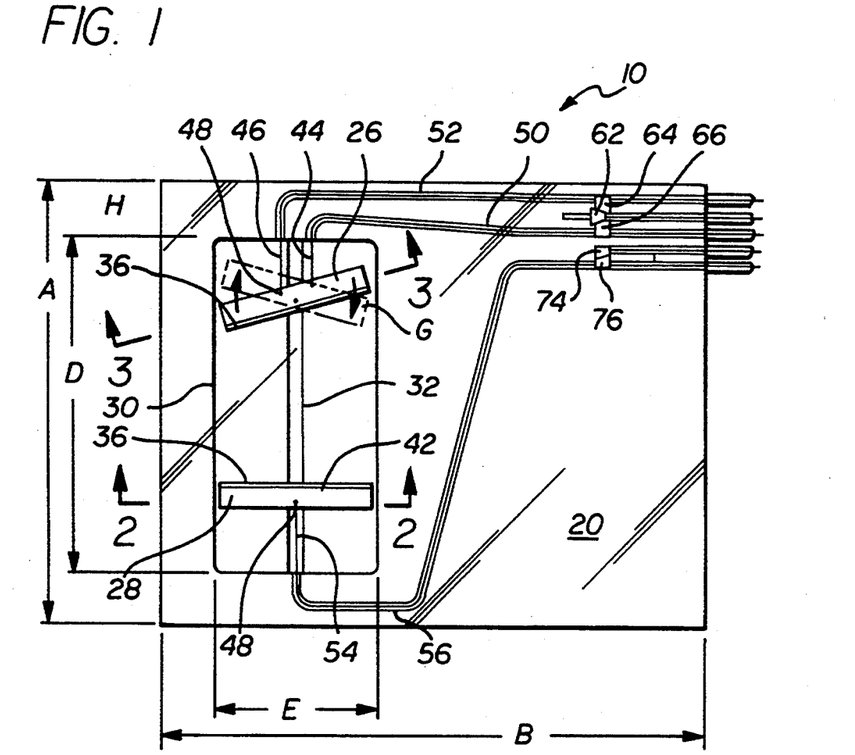
FIG. 1 is a top plan view of the first layer of the board of an embodiment of the invention.
Figure 2:
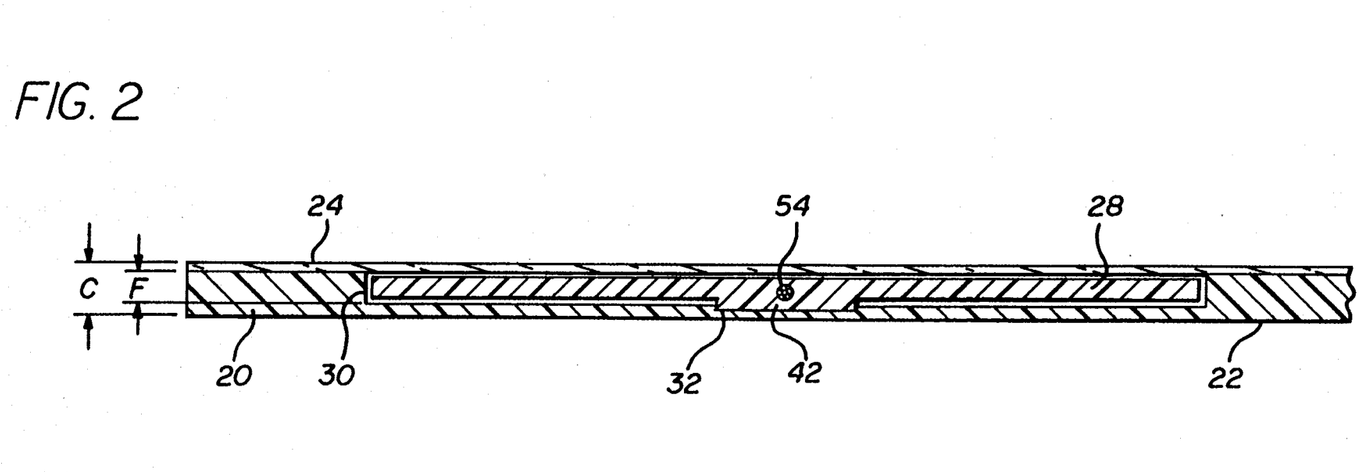
FIG. 2 is a cross-section taken along the line 2—2 of FIG. 1, showing a non-pivotable marker in the recessed region of the board.

Referring now to FIGS. 1–9, there is shown two embodiments of the marker system of the invention. In FIGS. 1 and 2, marker system 10 comprises marker board body 20 having first layer 22 and second layer 24. The board has length A of approximately sixteen inches (40.64 cms); width B of approximately twenty inches (50.8 cms); and height or depth C of approximately ⅜ of an inch (0.95 cm). The first and second layers are manufactured from polycarbonate or acrylonitrile-butadiene-styrene (ABS) thermoplastic. However, other materials can be used for the layers, such as any suitably strong non-radiopaque material. It is beneficial if the material of the second layer is transparent or highly translucent, so that the first or pivotable marker 26 and second or non-pivotable marker 28 can be roughly positioned in the general area where the patient's abdominal aortic bifurcation is expected to be, without the aid of fluoroscopy, before a catheterization procedure is commenced.

The first layer 22 of the marker board body 20 has recessed region 30 with length D of about twelve inches (30.48 cms); width E of about six inches (15.24 cms); and height or depth F of about 0.25 inch (0.64 cm). Track 32 is cut into the bottom of the recessed region at about the midpoint along its width and runs along the entire length of the recessed region. Positioners or marker control cables 44, 46 and 54 are disposed in the track and are connected to pivotable marker 26 and non-pivotable marker 28, respectfully. The control cables may be made from stainless steel, other strong metals, plastics, and nylons or similar non-radiopaque materials.

The main portion of both pivotable marker 26 and non-pivotable marker 28 is constructed of similar material as first board layer 22 or second board layer 24 and have a rectangular shape. Other suitable non-radiopaque materials and shapes also could be used. Both markers have a length of just under six inches (15.24 cms); a width of about one inch (2.54 cms) and a height or depth of about 3/16 of an inch (0.48 cm). The depth of the markers is such that neither marker extends above the height of the recessed area. Each marker has a radiopaque strip or rod 36 affixed to the edge of the marker oriented towards the center of recessed region 30. The radiopaque rods run along the entire width of the markers and are about 0.02 inches (0.05 cm) in diameter or thickness. Suitable radiopaque materials for the strips or rods include, but are not limited to, tungsten, gold and platinum.

The overall dimensions of marker board body 20 of marker system 10 are not critical, and merely should be suitable to allow the board to be easily positioned on an operating table. However, the length of recessed region 30 should be such to allow the pivotable marker 26 and non-pivotable marker 28 to be moved for distances that are relative to the distances of interest in the vasculature, for example, between the aortic bifurcation and the renal arteries. Similarly, the markers should be wide enough so that the board can be easily positioned under the aorta.

Figure 3:
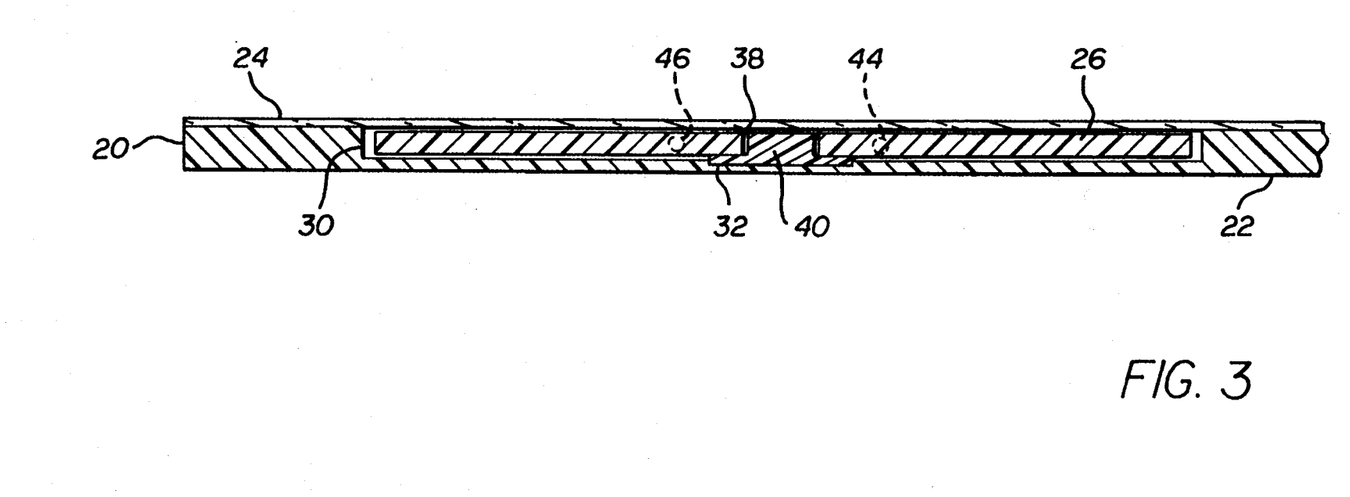
FIG. 3 is a cross-section taken along the line 3—3 of FIG. 1, showing a pivotable marker in the recessed region of the board.
Figure 8:
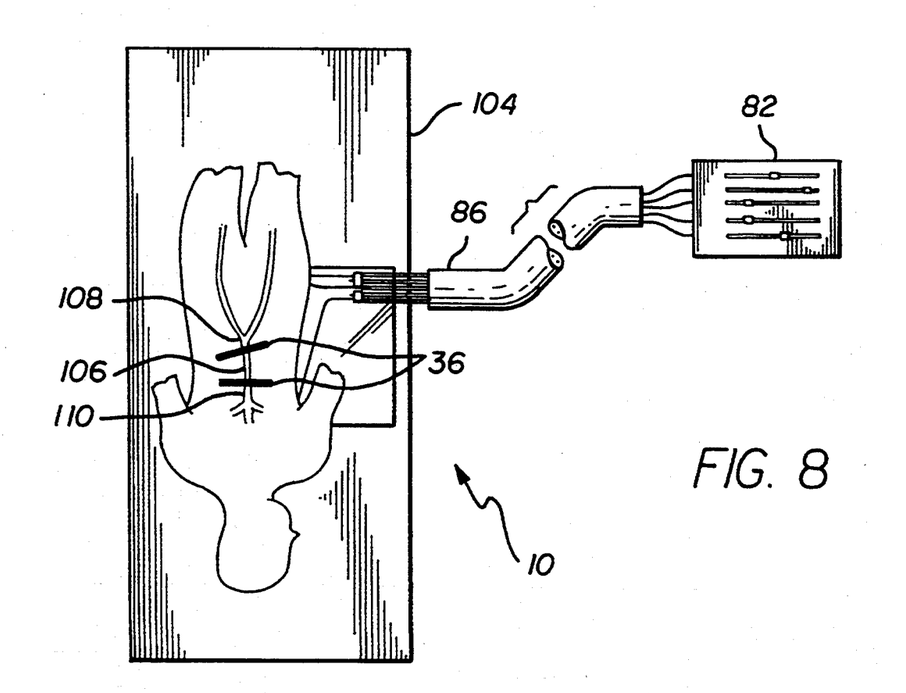
FIG. 8 is a schematic view of the marker system of FIG. 7 after a patient has been positioned on the operating table and the markers have been aligned.

Referring to FIG. 8, when board 20 is positioned, pivotable marker 26 will be oriented towards region 108 of the abdominal aorta closest to the aortic bifurcation. Since this region most frequently is where the vessel would be angled, the pivotable marker is provided to give the clinician a target that is perpendicular to the axis of the vessel. Accordingly, pivotable marker 26 is configured with a recess 38 to slip over pivot guide 40, as shown in FIG. 3. This configuration allows the pivotable marker both to move axially along the track 32 and to rotate about the pivot guide in the direction of arrows G and H. As non-pivotable marker 28 is less likely to be used to mark a position in an angled portion of a vessel, it is configured with a fixed guide 42. The marker is prevented from moving in any direction other than forward and backward along the track 32.

First pivot control cable 44 and second pivot control cable 46 are attached to pivotable marker 26 at ball swivel joints 48 and are disposed within the track 32. Other suitable connection devices may be used to secure the control cables to the pivotable marker. The cables extend from recessed region 30 to the exterior of the marker board body 20 in additional recessed regions or grooves 50 and 52. When the first pivot control cable is pushed or pulled by an operator from outside the board separately from the second pivot control cable, the pivotable marker will pivot or rotate about the pivot guide 40 in the direction of arrow G. When the second pivot control cable is similarly manipulated, the pivotable marker will pivot or rotate in the direction of arrow H. When both pivot control cables are moved together and at the same time, the pivotable marker will move forward or backward or axially along the track.

Marker control cable 54 is connected to non-pivotable marker 28 with a threaded adapter 49. Other suitable connection devices may be used. Control cable 54 is disposed in track 32 and to the exterior of the marker board body 20 in groove 56. The non-pivotable marker may by moved along the track by pushing or pulling the end of the cable exterior of the marker board body.

Figure 4:
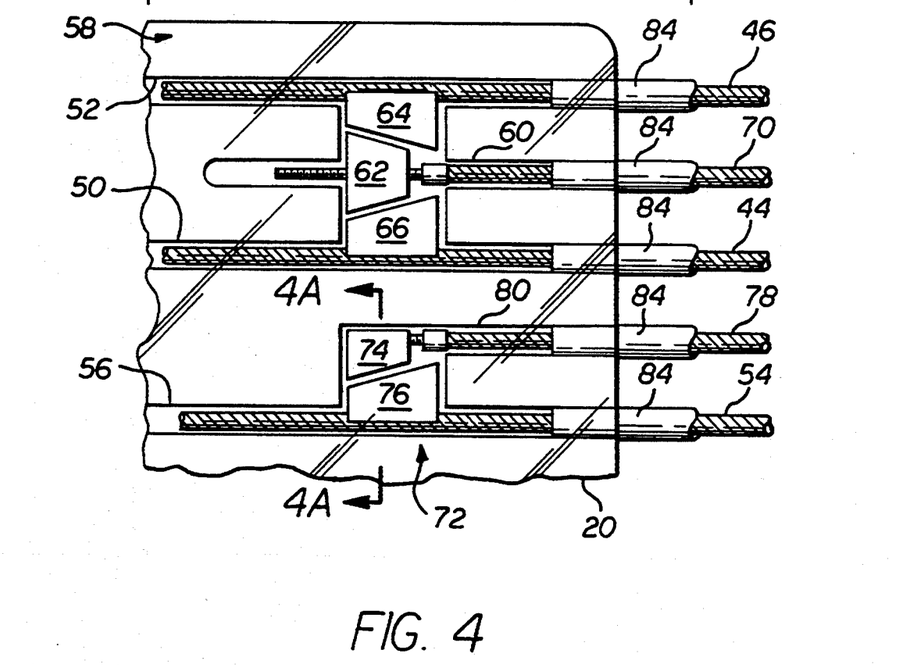
FIG. 4 is a partial, top view of an embodiment of the brakes in communication with the control cables.
Figure 4A:
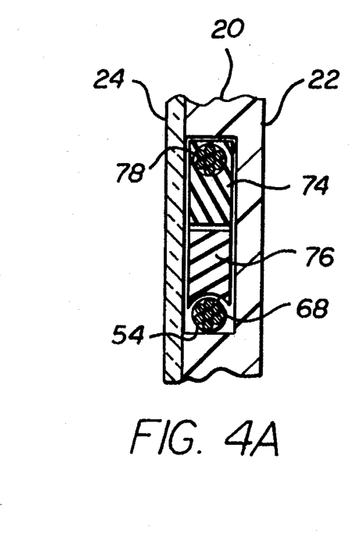
FIG. 4A is a cross-section taken along the line 4A—4A of FIG. 4.

Referring now to FIG. 4, there is shown dual braking element 58 for temporarily locking, holding or fixing the pivot control cables 44 and 46 into particular positions so that the pivotable marker 26 will stay in position throughout a catheterization procedure. The dual braking element is sufficient to lock both pivot control cables in a particular position. The braking element is disposed in recess 60 configured between pivot control cable grooves 50 and 52. The braking element comprises a trapezoidal shaped brake actuator 62 and two brake shoes 64 and 66. Each brake shoe extends into the control cable groove and has an indentation 68, which is configured to receive one of the control cables (FIG. 4A).

Brake actuator 62 is connected to brake cable 70, which also may be configured from a stainless steel wire or other suitable material. The side of each brake shoe 64 and 66 in contact with the brake actuator is angled to couple with the angled side of the actuator. When the brake cable is pulled away from the marker board body 20, the two brake shoes 64 and 66 are pushed away from the brake actuator. As the brake shoes are pushed by the actuator, the brake shoes clamp down on the pivot control cables 44 and 46 in the grooves 50 and 52. Thus, the control cables are prevented from moving and the pivotable marker 26 is locked into position. The brake is unlocked by pushing the brake cable toward the marker board body, thereby moving the brake actuator away from the brake shoes.

A single braking element 72 is provided to temporarily lock, hold or fix into position control cable 54, which is connected to non-pivotable marker 28. The single braking element is disposed in groove 80 of the marker board body 20 and comprises brake actuator 74, brake shoe 76 and brake cable 78. Indentation 68 in the brake shoe is configured to receive the marker control cable. Thus, when the brake cable is pulled, the brake shoe engages the control cable and prevents it from moving, thus locking the non-pivotable marker into place. The single brake is released by pushing the brake cable towards the marker board body, thereby moving the brake actuator away from the brake shoe.

Figure 5:
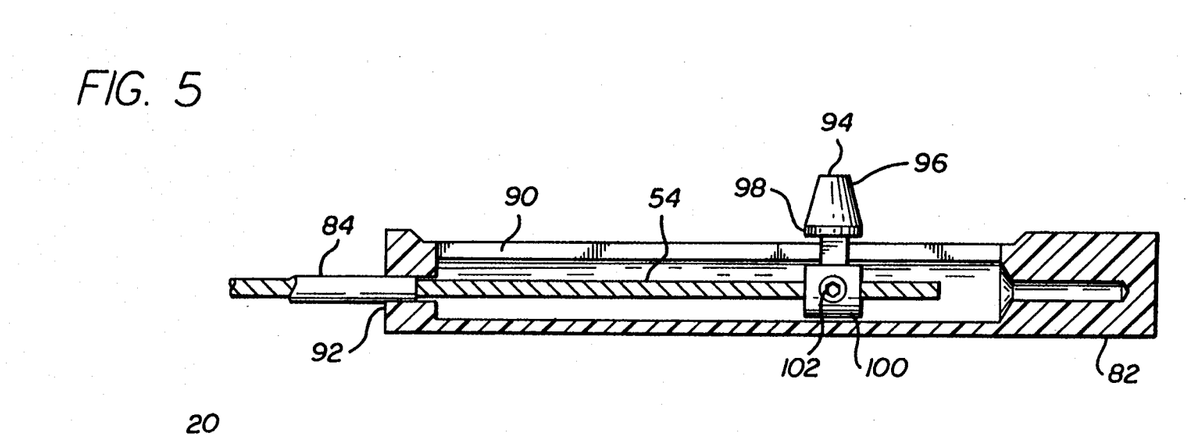
FIG. 5 is a cross-sectional side view of a control box, showing the termination and knob for one of the control cables.

Referring now to FIG. 5, control box 82 is connected to the ends of the control and brake cables which extend beyond the marker board body 20. Marker control cables 46, 44 and 54 and brake cables 70 and 78 are encased in sleeves 84, to provide additional rigidity to the cables so that they can be more easily pushed and pulled. The sleeves are preferably made of "TEFLON", a material manufactured by the E. I. duPont deNemours Company, but can be made of any other strong lubricous material. The sleeves for the marker control cables run from the point where the cables enter the recessed area 30 to the point where the cables enter the control box. The sleeves for the brake cables run from the brake actuators 62 and 74 to the point where the cables enter the control box.

Sheath 86, also preferably constructed of "TEFLON", encases all five cables from the point the cables exit the marker board body 20 to the point where the cables enter the control box 82. The sheath prevents the portions of the cables outside of the marker board body from becoming twisted, tangled or separated. The cables are generally concentric with the sleeves, and the sleeves are arranged in an approximately circular pattern within the sheath.

The top surface of control box 82 is fitted with slots 90 for each marker and brake cable. Cable openings 92 are provided at each slot for marker control cables 46, 44 and 54 and brake cables 70 and 78 to enter the control box. Thus, each of the cables are disposed in the control box within a slot. Position knobs 94 are provided for moving each cable. Each position knob has a top portion 96 having a base 98, and a bottom portion 100. Each marker control cable and brake cable is fastened to a positioning knob at connection point 102. The bases of the top portions of the positioning knobs are wider than the slots, so the control cables and brake cables remain suspended in about the center of the cable openings in the control box. When a particular positioning knob is moved along a slot, the control cable or brake cable attached to the positioning knob is pushed into or out of marker board body 20 and the respective marker or brake actuator is similarly moved.

Figure 6:
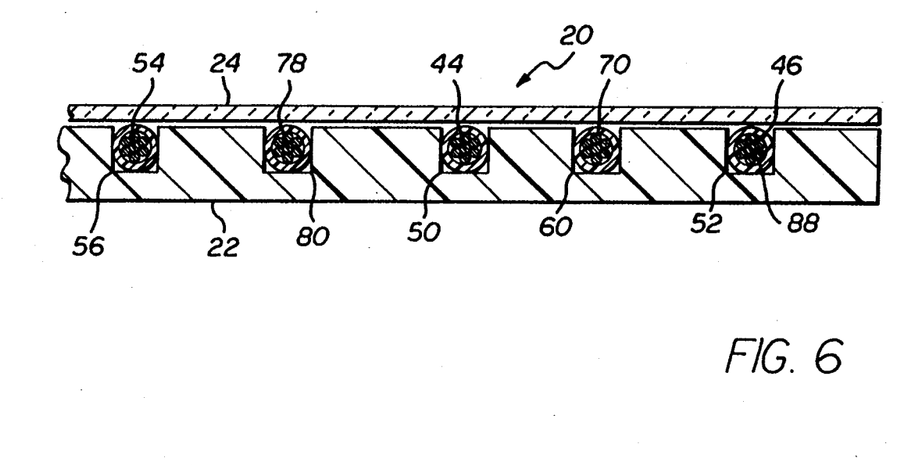
FIG. 6 is a cross-sectional side view of the board of the embodiment of FIG. 1, showing the entry points in the first layer for the control cables and brake cables.

FIG. 6 shows a side view of the cable entry points in the first layer 22 of the marker board body 20. Second board layer 24 is shown resting on top of the first layer. The control cable grooves 50, 52, and 56 extend from the recessed region 30 to one edge of the marker board body. Similarly, the brake cable grooves 60 and 80 extend from the brakes to the same edge of the marker board body. The dual brake cable groove 60 is between marker cable grooves 50 and 52 provided for pivot control cables 46 and 44. The single brake cable groove 80 is between marker cable groove 50 and marker cable groove 56. Each cable has several filaments 88 that are provided to add strength to the cables. The filaments are provided for each marker cable and brake cable.

Figure 7:
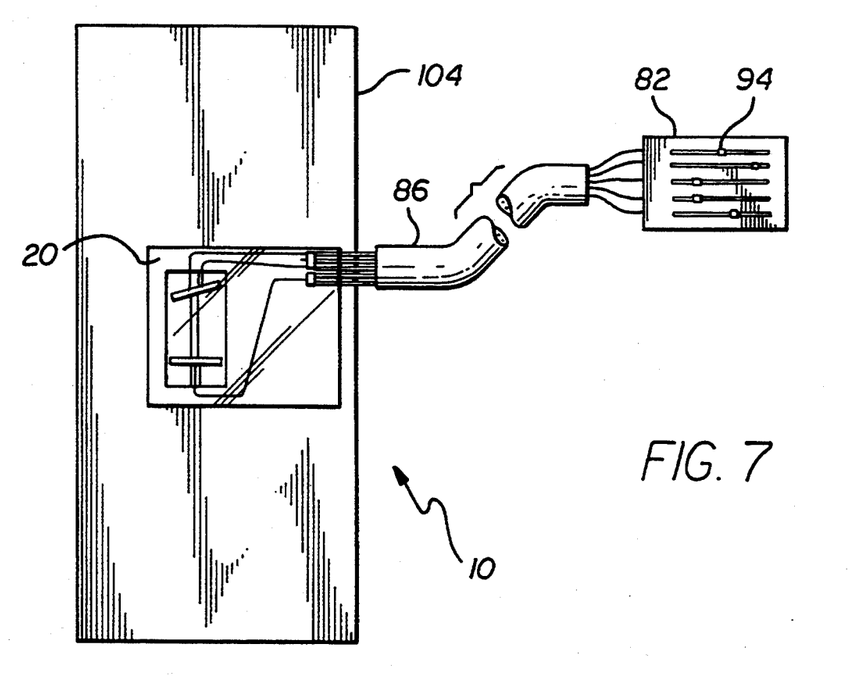
FIG. 7 is a schematic view of the embodiment of a marker system of the present invention prior to use with a patient.

Referring now to all of the figures and especially to FIGS. 7 and 8, and by way of example, a method of using the preferred embodiment of the marker system of the present invention in a procedure to implant an intraluminal graft at the site of an abdominal aneurysm is described. First, marker board body 20 is placed on an operating table 104 such that when the patient is positioned on the table, track 32 will be under the area where the abdominal portion of the patient's aorta 106 is expected to be. When the patient has been anesthetized to prevent movement, a fluoroscope or other radiographic imaging means is put into operation and the blood vessels in the area of interest are temporarily and fleetingly illuminated by the injection of radiopaque contrast fluid in that area. If digital subtraction imaging technology is available to the physician, an image might be captured at this point to be used for "roadmapping" later in the procedure.

During or immediately after the time the vessels are detectable, control cable 54 is pushed or pulled to move non-pivotable marker means 28 so that it indicates the location at which the anchoring means of the graft which is to be anchored to the vessel wall in the portion 110 of the abdominal aorta that is closest to the renal arteries. Then pivotable marker 26 is positioned by pushing or pulling control cables 44 and 46 at the same time to mark the anchor site for the anchoring means of the graft which is to be anchored to the vessel wall in the portion 108 of the abdominal aorta that is closest to the aortic bifurcation. If the patient's anatomy is such that the portion 108 of the abdominal aorta closest to the aortic bifurcation presents at an angle when illuminated by the dye, then control cables 44 and 46 can be manipulated separately to rotate the marker 26 about pivot guide 40 to reflect the angle of the vessel. Each of the marker control cables then can be temporarily locked into position with braking elements 58 and 72 by moving brake cables 70 and 78 with positioning knobs 94. Consequently, even though the radiopaque contrast fluid may have dispersed through the patient's circulatory system, radiopaque rods 36 of the markers 26 and 28 allow the physician to identify the proximal and distal bounds of the implantation site with substantial accuracy. By noting the relative positions of the radiopaque markers and the radiopaque tags which are provided on the catheter tip or the graft itself, the physician then can proceed to deploy an intraluminal graft using standard catheterization techniques well known in the art.

Figure 9:
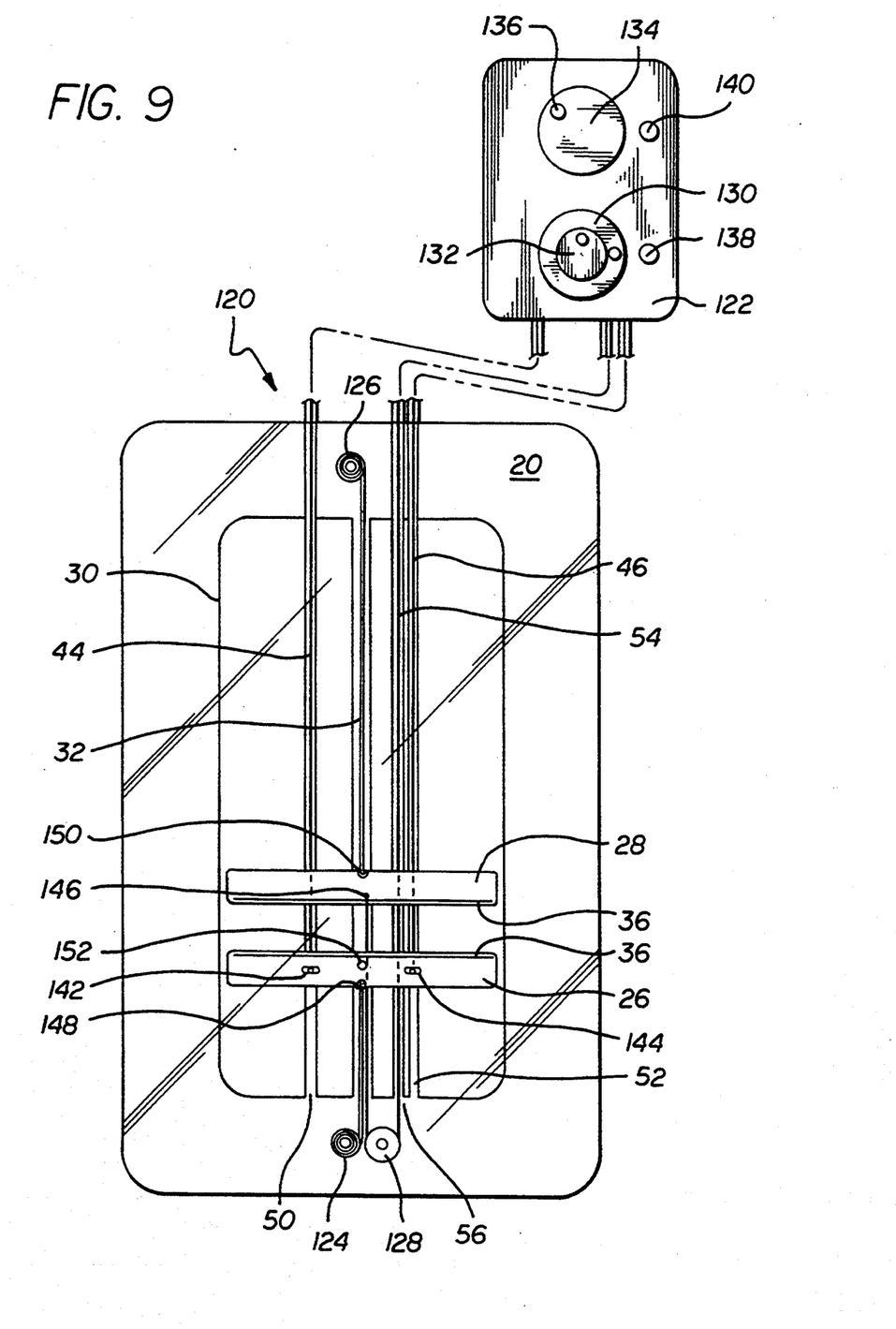
FIG. 9 is a top plan view of an alternative embodiment of the invention.

FIG. 9 shows an alternative embodiment of the marker system of the invention. The marker system 120 comprises a marker board body 20 and a control box 122. The marker board body comprises a polycarbonate plate which is configured to reside on an operating table under a patient pad and is used to house two movable markers 26 and 28. The control box is used to remotely move the position the markers which are biased against movement by two constant force springs 124 and 126.

The marker board body 20 comprises two layers, having an overall thickness of approximately ¾ of an inch (1.91 cm). A recessed region 30 has been provided to allow clearance for the movable components and is approximately ⅛ of an inch (−0.32 cm) deep. Three grooves 50, 52 and 56 in the marker board body provide clearance for the control cables 44, 46, 54 and extend from the caudal end of the recess region to the cranial end of the marker board body. Additional recesses are provided for the two constant force springs 124 and 126, and a pulley 128. The top layer of the marker board body is a solid sheet of polycarbonate and is attached to the bottom layer using nylon screws (not shown).

The control box 122 is attached to the marker board body 20 with semirigid plastic tubing (not shown). The nylon control cables 44, 46 and 54 are disposed in the plastic tubing and are connected to three control wheels 130, 132 and 134. Each of the control wheels have a knob or finger grip 136 used to rotate the control wheel. The control box further has two brakes 138 and 140 to lock the control cables in place, thus locking the markers 26 and 28 at a desired position in the marker board body.

The markers 26 and 28 comprise tungsten rods 36 mounted in or on polycarbonate holders. The markers are partially disposed in a central slot or track 32 that runs the length of the recessed region 30 in the marker board body 20. The caudal or pivotable marker is attached to a first constant force spring 124 and two control cables 44 and 46. The constant force spring for the caudal marker is positioned at the caudal end of the marker board body and is attached to the marker at a point 148 near the track on the caudal side of the marker. Each of the control cables for the caudal marker are connected at one end at points 142 and 144 on the marker at either side of the track.

The cranial or non-pivotable marker 28 is attached to a second constant force spring 126 and a control cable 54, which is wrapped around a pulley 128 located at the caudal end of the marker board body 20. The constant force spring for the cranial marker is positioned at the cranial end of the marker board body and is attached to the marker at a point 150 on the cranial side of the marker. The control cable for the cranial marker is attached on the caudal side of the marker at a point 146 near the track.

The ends of the control cables 44, 46 and 54 which are not attached to the markers 26 and 28 are attached to and wound around the control wheels 130, 132 and 134. When a control wheel is rotated in one direction, the respective control cable is shortened, thereby pulling the marker against the respective constant force spring and towards the medial portion of the marker board body 20. During the control wheel rotation, the constant force spring uncoils, creating a biasing force which holds the control cable in tension. When a control wheel is turned in the opposite direction, the control cable lengthens and the constant force spring pulls the marker away from the medial portion of the marker board body, maintaining the tension in the control cable.

The caudal marker 26 is actuated using two control cables 44 and 46. Two control cables provide linear and rotational movement of the marker. The caudal marker control cables are connected to the control wheels 130 and 132 in control box 122. The two control wheels are mounted coaxially and can be simultaneously actuated by rotating the outer wheel. Simultaneous rotation of the wheels moves the caudal marker linearly along the track. Differential turning of the inner and outer caudal control wheels rotates the caudal marker about the pivot point 152 located at the track. Similarly, the cranial marker 28 is actuated using one control cable 54 to move the marker linearly along the track 32 in the marker board body.

While particular forms of the invention have been illustrated and described, it also will be apparent to those skilled in the art that various modifications can be made without departing from the spirit and scope of the invention. For example, the system of the invention likely can be used with great success in procedures other than those performed for the purpose of implanting intraluminal grafts. It is not intended that the invention be limited except as by the appended claims.

What is claimed is:

1. Apparatus for use in radiography and fluoroscopy, the apparatus comprising:
    a body having a recessed region;
    marker means rotatably disposed in the recessed region of said body, said marker means having radiopaque material; and
    control means disposed in the recessed region of said body and operably connected to said marker means for moving and rotating said marker means within said body.

2. The apparatus of claim 1, further comprising:
    second marker means disposed in the recessed region of said body, said second marker means having radiopaque material; and
    second control means disposed in the recessed region of said body and operably connected to said second marker means for moving said marker means within said body.

3. Apparatus for locating a position in the vasculature of a patient, the apparatus comprising:
    a non-radiopaque body;
    a first radiopaque marker disposed in said body;
    a second radiopaque marker rotatably disposed in the said body;
    a first positioner means for moving said first marker relative to said second marker; and
    a second positioner means for moving and rotating said second marker relative to said first marker, said second positioner means adapted to rotate said second marker relative to said first marker independently of moving said second marker relative to said first marker.

4. The apparatus of claim 3, further comprising a first brake for fixing said first marker stationary relative to said second marker.

5. The apparatus of claim 4, further comprising a second brake for holding said second marker stationary relative to said first marker.

6. The apparatus of claim 3, wherein said body includes a first layer and a second layer, wherein said first marker, said first positioner means, said second marker and said second positioner means are disposed within at least one recessed region within the first layer of said body, and said second layer is configured to cover the recessed region of the first layer of said body.

7. The apparatus of claim 5, further comprising means connected to said first positioner means, said second positioner means, said first brake and said second brake for manipulating each of said positioner means and said brakes.

8. The apparatus of claim 3, further comprising means connected to said first marker for biasing said first marker from movement by said first positioner means.

9. The apparatus of claim 8, further comprising means connected to said second marker for biasing said second marker from movement by said second positioner.

10. Apparatus configured to be positioned beneath the body of a patient for use with a catheter to assist in locating a position in the vasculature of a patient for the purpose of making a diagnosis or rendering treatment therein, the apparatus comprising:
    a board having a first layer and a second layer disposed over the first layer, the first layer having a track configured therein;
    a marker at least partially formed of a radiopaque material, said marker being configured to move axially along the track of the first layer of said board; and
    a control cable having a first end attached to said marker for moving said marker along the track of the first layer of said board, said control cable having a second end,
    wherein the second layer of said board is configured to prevent said marker and said control cable from contacting a patient.

11. The apparatus of claim 10, further comprising braking means for locking said control cable and said marker into a desired position.

12. The apparatus of claim 11, wherein said braking means comprises a brake shoe configured to contact said control cable, a brake actuator configured to contact the brake shoe, a brake cable having a first end attached to the brake actuator and having a second end, wherein moving the brake cable causes the brake actuator to move the brake shoe into contact with said control cable and to fix the control cable in place.

13. The apparatus of claim 11, further comprising manipulating means connected to the second end of said control cable for causing movement of said marker along the track of the first layer of said board and connected to said braking means for actuating said braking means.

14. The apparatus of claim 13, wherein said manipulating means is connected to said control cable and said braking means exterior to said board.

15. The apparatus of claim 14, wherein the manipulating means further comprises a control box configured to receive the second end of said control cable and said braking means, wherein the control cable and braking means may be manipulated from the control box.

16. The apparatus of claim 10, wherein said control cable is formed from stainless steel.

17. The apparatus of claim 10, wherein said control cable is formed from an non-radiopaque material.

18. The apparatus of claim 10, further comprising;
a second marker at least partially formed of a radiopaque material, said second marker having a guide configured to move along the track of the first layer of said board, said second marker being pivotable about the guide;
a second control cable having a first end attached to said second marker and having a second end; and
a third control cable having a first end attached to said second marker and having a second end,
wherein said second control cable and said third control cable are attached to said second marker for moving the second marker along the track in an axial direction and for pivoting said second marker about the guide.

19. The apparatus of claim 10, further comprising a constant force spring attached to said marker, wherein said constant force spring biases said marker from the movement of said control cable.

20. Apparatus for use in fluoroscopy and configured to be positioned beneath the body of a patient, the apparatus comprising:
a board having a first layer and a second layer disposed over the first layer, the first layer having a track configured therein;
a first marker including radiopaque material, said first marker being configured to move axially along the track of the first layer of said board;
a second marker including radiopaque material, said second marker being configured to move axially along and rotate about the track of the first layer of said board;
a first control cable having a first end attached to said first marker for moving said first marker along the track of the first layer of said board;
a second control cable having a first end attached to said second marker for moving and rotating said second marker along the track of the first layer of said board;
a third control cable having a first end attached to said second marker for moving and rotating said second marker along the track of the first layer of said board;
first braking means for locking said first control cable and said first marker into a desired position; and
second braking means for locking said second control cable, said third control cable and said second marker into a desired position,
wherein the second layer of said board is configured to prevent said markers and said control cables from contacting a patient.

21. The apparatus of claim 20, further comprising a first constant force spring attached to said first marker, wherein said first constant force spring biases said first marker from the movement of said first control cable, and a second constant force spring attached to said second marker, wherein said second constant force spring biases said second marker from the movement of said second control cable and said third control cable.

* * * * *

UNITED STATES PATENT AND TRADEMARK OFFICE
CERTIFICATE OF CORRECTION

PATENT NO. : 5,419,324
DATED : May 30, 1995
INVENTOR(S) : David C. Dillow

It is certified that error appears in the above-indentified patent and that said Letters Patent is hereby corrected as shown below:

Column 10, Claim 9, Line 40, After "positioner", add --means--.

Signed and Sealed this

Twenty-third Day of September, 1997

Attest:

BRUCE LEHMAN

Attesting Officer

Commissioner of Patents and Trademarks